United States Patent [19]

Bousquet et al.

[11] Patent Number: 5,132,435
[45] Date of Patent: Jul. 21, 1992

[54] 2-THIENYLGLYCIDIC DERIVATIVE, PROCESS FOR ITS PREPARATION AND ITS USE AS SYNTHESIS INTERMEDIATE

[75] Inventors: Andre Bousquet; Serge Calet; Alain Heymes, all of Sisteron, France

[73] Assignee: Sanofi, Paris, France

[21] Appl. No.: 724,988

[22] Filed: Jul. 2, 1991

[30] Foreign Application Priority Data

Jul. 4, 1990 [FR] France .................. 90 08482

[51] Int. Cl.$^5$ .................. C07D 407/04; C07D 333/22; C07D 495/04
[52] U.S. Cl. ........................... 549/60; 546/114; 549/75
[58] Field of Search ................. 549/60, 75; 546/114

[56] References Cited

FOREIGN PATENT DOCUMENTS 0069002 1/1983 European Pat. Off. .

OTHER PUBLICATIONS

Dullaghan et al., I, J. O. C., 17, pp. 1183-1186 (1952).
Dullaghan et al., II, J. O. C., 18, pp. 878-881 (1953).
Patent Abstracts of Japan, vol. 11, No. 317, (C-452) (2764), Oct. 15, 1987; & JP-A-62 103 087, (Toyo Pharma K.K.), May 15, 1987.
Chemical Abstracts of Japan, vol. 89, No. 3, Jul. 17, 1978, p. 650; & JP-A-53 07 687, (Sanwa Chemical Laboratories), Jan. 24, 1978.

*Primary Examiner*—Bernard Dentz
*Attorney, Agent, or Firm*—Wegner, Cantor, Mueller & Player

[57] ABSTRACT

The invention relates to isopropyl 2-thienylglycidate of formula:

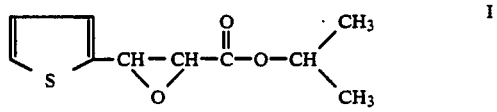

obtained by reaction of 2-thienylcarboxaldehyde with an isopropyl haloacetate. It is employed as a synthesis intermediate in the preparation of 2-thienylacetaldoxime and of medications derived from thieno[3,2-c]pyridine.

10 Claims, No Drawings

2-THIENYLGLYCIDIC DERIVATIVE, PROCESS FOR ITS PREPARATION AND ITS USE AS SYNTHESIS INTERMEDIATE

The present invention relates generally to a new 2-thienylglycidic derivative, to a process for its preparation and to its use as synthesis intermediate.

More precisely, a further subject of the invention is isopropyl 2-thienylglycidate of formula:

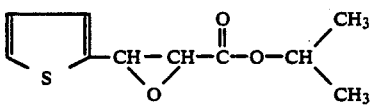

The compound of the invention has been found particularly useful as an intermediate product especially for the preparation of 2-thienylacetaldoxime. The latter can itself be widely employed as an intermediate in the preparation of various products, especially for the final synthesis of thieno[3,2-c]pyridine derivatives, of general formula:

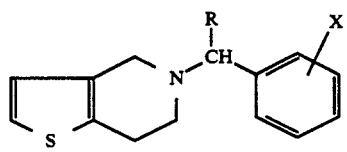

in which R denotes hydrogen or a

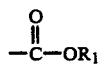

radical in which $R_1$ denotes a $C_1$-$C_4$ alkyl radical such as methyl and X denotes hydrogen or a halogen atom such as chlorine, and of their pharmaceutically acceptable salts.

Such thieno[3,2-c]pyridine derivatives, either in the form of racemic mixture or of separated enantiomers, have been described especially in French Patents Nos. 2,215,948, 2,530,247 and 2,612,929.

These compounds have been found particularly advantageous for their therapeutic applications, especially for their platelet antiaggregating and anti-thrombotic properties.

Among the most advantageous thieno[3,2-c]pyridine derivatives of formula Ia there may be mentioned 5-(2-chlorobenzyl)-4,5,6,7-tetrahydrothieno[3,2-c]pyridine or ticlopidine (INN) and methyl α-(4,5,6,7-tetrahydro-5-thieno[3,2-c]pyridyl) (2-chlorophenyl)acetate, more particularly in the form of its dextrorotatory enantiomer or clopidogrel (INN).

A process for the preparation of 2-(2-thienyl)ethylamine comprising the following stages has been described in Patent FR-A-2,508,456:

a) the conversion of 1-nitro-2-(2-thienyl)ethylene into 2-thienylacetaldoxime by catalytic hydrogenation over palladium to give 2-thienylacetaldoxime which is isolated from its reaction mixture, and b) reduction of this oxime to 2-(2-thienyl)ethylamine by hydrogenation in the presence of a catalyst, namely Raney nickel.

While the second stage can be carried out under conditions similar to those generally employed for the reduction of imines, that is to say in an ammonia-saturated alcoholic solvent, the application of the first stage is found to be more tricky. In fact, 1-nitro-2-(2-thienyl)ethylene is sensitive both to acidic and basic media.

In a basic medium this compound can lead to the formation of dimeric or polymeric compounds, while in an acidic medium the opening of the thiophene nucleus to give mercaptans (catalyst poison) and dehydration of the oxime formed to the corresponding nitrile can be observed.

According to an application described in this patent, the reduction of 1-nitro-2-(2-thienyl)ethylene is carried out especially in a 75/25 acetic acid/ethanol medium in the presence of 1% of palladium in metallic form and at a dilution of 5%, and this gives 2-thienylacetaldoxime in oily form in a 60% yield.

It is known, furthermore, that the oxime functional group can be generally obtained by reaction of an aldehyde functional group with hydroxylamine and this, in the present case, would make it possible to assume that 2-thienylacetaldoxime is obtained from 2-thienylacetaldehyde.

A method for preparing this aldehyde has been described in J. Org. Chem. 17 pp. 1183-1186 (1952) and 18 pp. 878-881 (1953), according to which 2-thienylcarboxaldehyde is reacted with methyl chloroacetate in the presence of sodium methylate in ethyl ether, and this gives methyl 2-thienylglycidate in a 64% yield.

This glycidic derivative is then saponified with sodium hydroxide in ethanol and is then decarboxylated by heating to 2-thienylacetaldehyde, the best yields being obtained after first acidifying the reaction mixture.

The overall yield of this process for the preparation of 2-thienylacetaldehyde, namely 12% based on 2-thienylcarboxaldehyde, makes it consequently possible to assume that 2-thienylacetaldoxime can apparently be obtaine from 2-thienylacetaldehyde thus prepared only in a maximum yield of 12%, whatever the method employed for applying hydroxylamine or 2-thienylacetaldehyde.

The search for an industrial process for the preparation of 2-thienylacetaldoxime employing easily accessible and inexpensive synthesis intermediates and a satisfactory yield of final product remains undoubtedly of interest.

It has now been found that isopropyl 2-thienylglycidate makes it possible to prepare 2-thienylacetaldoxime in question in yields of the order of 90%, that is to say far higher than those which could be obtained according to the previous technique.

Moreover, it has been found that isopropyl 2-thienylglycidate can itself be obtained in a remarkably advantageous manner and in yields which are very high, since they are better than 95%.

The invention consequently relates to isopropyl 2-thienylglycidate as a new industrial product useful especially as synthesis intermediate, for example for the preparation of 2-thienylacetaldoxime.

According to the invention, isopropyl 2-thienylglycidate is prepared by reacting 2-thienylcarboxaldehyde with an isopropyl haloacetate, for example isopropyl chloroacetate, in isopropanol and at room temperature, in the presence of an alkali metal isopropylate, preferably sodium isopropylate.

According to a preferred embodiment of the invention, isopropyl 2-thienylglycidate is obtained by introducing a mixture of 2-thienylcarboxaldehyde and isopropyl chloroacetate into a mixture of isopropanol and of an alkali metal isopropylate, for example sodium isopropylate.

As mentioned above, isopropyl 2-thienylglycidate can give access to 2-thienylacetaldoxime.

Consequently, another subject of the invention relates to the preparation of 2-thienylacetaldoxime by using a process according to which:
a) isopropyl 2-thienylglycidate is saponified with an alkali metal hydroxide, and this yields the corresponding alkali metal glycidate, and
b) this alkali metal glycidate is treated, after being or not being isolated from its preparation medium, with an aqueous solution of a hydroxylamine salt, for example hydrochloride or sulphate, the reaction taking place at room temperature,
which yields the desired 2-thienylacetaldoxime.

The saponification generally takes place in an organic solvent such as a $C_1$–$C_4$ alcohol and at a temperature between room temperature and the reflux temperature of the reaction mixture, preferably at a temperature of the order of 40° to 60° C.

Furthermore, the alkali metal hydroxide is preferably sodium or potassium hydroxide and the hydroxylamine salt is preferably in the form of hydrochloride.

According to a preferred embodiment, 2-thienylacetaldoxime is prepared without isolation of the 2-thienylacetaldehyde formed temporarily.

According to a particularly advantageous alternative form of the invention, the preparation of 2-thienylacetaldoxime is carried out via isopropyl 2-thienylglycidate in the actual medium in which this ester is prepared.

Consequently, according to an alternative form of the invention, 2-thienylacetaldoxime is prepared by a process using the following stages:
a) 2-thienylcarboxaldehyde is reacted in isopropanol and at room temperature to obtain, temporarily and without isolation, isopropyl 2-thienylglycidate, and
b) the ester obtained is saponified with an alkali metal hydroxide and at a temperature between room temperature and the reflux temperature of the mixture, and is then treated at room temperature with an aqueous solution of a hydroxylamine salt and this, after a decarboxylation reaction, yields the desired oxime.

As indicated above, isopropyl 2-thienylglycidate can be employed for the preparation of thieno[3,2-c]pyridine derivatives of formula Ia.

Consequently, the invention also relates to isopropyl 2-thienylglycidate as an intermediate for the final synthesis of thieno[3,2-c]pyridine derivatives of formula Ia, in particular for the synthesis of ticlopidine and of clopidogrel.

For example, these compounds of formula Ia can be prepared from 2-thienylacetaldoxime, itself obtained according to the invention from isopropyl 2-thienylglycidate, by using a process comprising the following sequence of stages:
(a) this oxime is hydrogenated at a hydrogen pressure of between 1 and 100 atmospheres ($10^5$ and $10^7$ Pa), at a temperature of between 20° and 100° C. and in the presence of a basic agent such as ammonia and of a metallic catalyst such as Raney nickel, palladised charcoal or platinum black, to obtain 2-(2-thienyl)ethylamine, (b) the compound thus obtained is reacted with formaldehyde or paraformaldehyde, generally 1 to 1.5 moles per mole of starting compound, the reaction being carried out by heating to a temperature of 70° to 90° C. to obtain 2-(2-thienyl)ethylamine formimine, (c) the compound thus formed is reacted with an acid such as hydrochloric acid and at a temperature of between 40° and 60° C. to obtain a 4,5,6,7-tetrahydrothieno[3,2-c]pyridine salt, for example the hydrochloride, which is optionally treated with a basic agent such as an alkali metal hydroxide to regenerate the thieno[3,2-c]pyridine derivative in basic form, (d) 4,5,6,7-tetrahydrothieno[3,2-c]pyridine in base or salt form is reacted, in the presence of an acid-acceptor, for example an alkali metal carbonate or bicarbonate, and optionally under phase transfer conditions, with a compound of general formula:

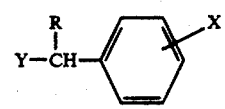

in which R and X have the same meaning as above and Y denotes a halogen atom such as chlorine or bromine or a $C_1$–$C_4$ alkylsulphonate group such as methanesulphonate or $C_6$–$C_{10}$ arylsulphonate such as benzenesulphonate or p-toluenesulphonate, the reaction preferably taking place at a temperature of 60° to 90° C. to obtain the desired compound of formula Ia which can be converted into a pharmaceutically acceptable salt by reaction with an appropriate organic or inorganic acid.

When R is other than hydrogen, the compound of formula Ia is obtained in the form of a mixture of enantiomers. These enantiomers can be separated by known methods, for example by recrystallisation of salts of optically active acids or by the application of a chromatographic technique.

The stages (a) to (d) above can be generally carried out in aqueous solution or in a polar organic solvent such as $C_1$–$C_4$ alcohol.

Stage (a) is carried out in a solvent saturated preferably with ammonia, while stage (b) can also take place in water, that is to say by starting with an aqueous formaldehyde solution.

As for stage (d), this can be carried out in an inert solvent such as $C_1$–$C_4$ alcohol, N,N-dimethylformamide, an ether such as tetrahydrofuran or isopropyl ether, or an ester such as ethyl acetate.

Furthermore, "phase transfer conditions" mean reaction conditions which take place in a two-phase solvent system and in the presence of a phase transfer catalyst.

The hydrocarbon/water or ether/water systems may be mentioned especially as two-phase solvent systems. As for the phase transfer catalyst, this may be, for example, a quaternary ammonium salt, a phosphonium salt or a crown ether.

Stages (a) to (d) above are known stages, which have been described in Patents FR-2,215,948, 2,508,456 and JP-63-101,385 (Chem. Abstr. 109, 92980q).

The following nonlimiting examples illustrate the invention:

EXAMPLE 1

Preparation of isopropyl 2-thienylglycidate

A solution of sodium isopropylate is prepared in a 250-ml round bottom flask by adding 3.6 g of sodium to 140 ml of isopropanol and then heating progressively to 80° C. for 30 minutes. The mixture is kept stirred until the sodium has been completely consumed. The reaction mixture is cooled to 20° C. and a mixture of 16.8 g of 2-thienylcarboxaldehyde and 22.55 g of isopropyl chloroacetate is introduced over 10 minutes. The solution is stirred for 25 minutes at this temperature and is then cooled to 5° to 10° C. This reaction mixture is then added to a mixture of 50 g of ice, 150 ml of water and 2 ml of acetic acid. It is extracted firstly with 150 ml and then with twice 75 ml of dichloromethane; the organic phases are combined and are dried over sodium sulphate. After filtration and evaporation of the solvents, 30.85 g of an orangy oil are obtained and this is distilled under a reduced pressure to give 29.6 g of a colourless liquid.

Isopropyl 2-thienylglycidate is obtained in this manner.

Yield: 93%.

B.p.: 105° C. (0.5 mm Hg or 66.5 Pa)

$n_D^{20} = 1.5170$

I.R. spectrum (film): 3100–3000 (aromatic —CH); 1735 (COO); 1250 (C—O—C) cm$^{-1}$ $^1$H NMR spectrum (CDCl$_3$) (300 MHz) of the (E) enantiomer $\delta = 1.29$ (6H,d,CH$_3$); 3.64 (1H,d,CH—O); 4.28 (1H,d,CH—O); 5.12 [1H,m,CH(CH$_3$)$_2$]; 6.97 (1H,m,aromatic CH); 7.17 (1H,d,aromatic CH); 7.27 (1H,d,aromatic CH) ppm.

$^1$H NMR spectrum (CDCl$_3$) (300 MHz) of the (Z) enantiomer $\delta = 1.12$ (6H,d,CH$_3$); 3.82 (1H,d,CH—O); 4.78 (1H,d,CH—O); 4.97 [1H,m,CH(CH$_3$)$_2$]; 6.97 (1H,m,aromatic CH); 7.17 (1H,d,aromatic CH); 7.27 (1H,d,aromatic CH) ppm.

EXAMPLE 2

Preparation of 2-thienylacetaldoxime 30.85 g of isopropyl 2-thienylglycidate in 140 ml of isopropanol are introduced into a round bottom flask. 25.7 g of a sodium hydroxide solution at a concentration of 35% w/v are then added over 5 minutes and the solution is then stirred for 2 hours at 50° C. It is cooled to 25° C. and 16.15 g of hydroxylamine hydrochloride dissolved in 20 ml of water are then introduced over 10 minutes. The mixture is kept stirred for 30 minutes and is then added to 150 ml of water and 150 ml of dichloromethane. It is extracted with twice 100 ml of dichloromethane, the organic phases are combined and are dried over sodium sulphate. After filtering the solvent is evaporated off.

20.16 g of crystalline 2-thienylacetaldoxime are obtained in this manner.

Yield: 95%

M.p.: 92° C.

I.R. spectrum (KBr): 3400–3100 (OH); 3100–3000 (aromatic=CH); 2855 (CH=N); 1655 (C=N) cm$^{-1}$ $^1$H NMR spectrum (DMSO-d$_6$) (300 MHz) $\delta = 3.68$ [2H,d,CH$_2$(Z)]; 3.84 [2H,d,CH$_2$(E)]; 6.62–6.91 [6H,m, aromatic protons (Z)+(E)]; 7.37 [1H,t,C(H)=N]; 10.71 [H,s,OH(Z)]; 11.1 [1H,s,OH (E)] ppm.

EXAMPLE 3

Preparation of 2-thienylacetaldoxime

A solution of sodium isopropylate is prepared in a 2.5-l reactor by adding 36 g of sodium to 1.4 l of isopropanol and heating progressively to 80° C. over 30 minutes. The mixture is kept stirred until the sodium has been completely consumed and is then cooled to 20° C.

A mixture of 168 g of 2-thienylcarboxaldehyde and 12.9 g of isopropyl chloroacetate is then introduced over 30 minutes. The solution is stirred for 25 minutes at this temperature and 257 g of an aqueous solution of sodium hydroxide at a concentration of 35% are then added over 30 minutes. The mixture is stirred at 50° C. for 2 hours, is cooled to 25° C. and 161.5 g of hydroxylamine hydrochloride dissolved in 200 ml of water are then introduced over 30 minutes. The mixture is kept stirred for 30 minutes and is then added to 1.5 l of water and 1.5 l of dichloromethane.

It is extracted with twice 1 l of dichloromethane, the organic phases are combined and are dried over sodium sulphate.

After filtration and evaporation of the solvents 191 g of crystalline 2-thienylacetaldoxime are obtained.

Yield: 90%

M.P. 92° C.

$^1$H NMR spectrum (DMSO-d$_6$) (300 MHz)$\delta = 3.68$ ppm [2H,d,CH$_2$(Z)]; 3.84 ppm [2H,d,CH$_2$(E)]; 6.62–6.91 ppm [3H,m, aromatic protons]; 7.37 ppm [1H,t,C(H)=N]; 10.71 ppm [H,s,OH(Z)]; 11.1 ppm [1H,s,OH(E)].

The following examples illustrate the preparation of ticlopidine and of clopidogrel.

EXAMPLE A

Preparation of 5-(2-chlorobenzyl)-4,5,6,7-tetrahydrothieno[3,2-c]pyridine hydrochloride a) 2-(2-Thienyl)ethylamine A 300 ml autoclave is purged with nitrogen before being evacuated and 100 ml of an isopropanol solution saturated with ammonia (11.1 g), 7.5 g of 2-thienylacetaldoxime prepared according to Example 3 above and 0.7 g of Raney nickel catalyst (1 g wet) are introduced.

The whole is placed under a pressure of 20 bars of hydrogen (2×10$^6$ Pa) and the temperature is raised to 50° C. over 20 minutes while stirring of the reaction mixture is continued. Hydrogen is topped up to 20 bars at regular intervals as it is consumed until no more is absorbed (approximately 6 hours).

The catalyst is then filtered off, is rinsed with isopropanol and an analysis of the starting material is carried out by gas phase chromatography with internal standardisation.

2-(2-Thienyl)ethylamine is obtained in this manner.

Yield: 91.5%.

b) 2-(2-Thienyl)ethylamine formimine 181 g of 2-(2-thienyl)ethylamine are charged into a 500-ml three-necked round bottom flask fitted with a thermometer, a condenser, a mechanical stirrer and a dropping funnel. 130 g of an aqueous solution of formalin at a concentration of 35% are added over 10 minutes. As soon as the addition of the formalin commences the reaction mixture assumes a milky appearance and its temperature rises steadily to reach 90° C. It is stirred for 30 minutes before 300 ml of toluene and 100 ml of an aqueous solution of sodium chloride at a concentration of 10% are introduced. After phase separation the aqueous phase is reextracted with twice 100 ml of toluene, and the toluene phases are combined and are washed with twice 100 ml of water saturated with sodium chloride. After evaporation of the toluene 198 g of oil are obtained, which crystallises at 0° C. to give 2-(2-thienyl)ethylamine formimine in a 100% yield.

M.p.=49° C.
¹H NMR spectrum (DMSO-d₆) (300 MHz)
δ=2.7–3.0 (4H,m,CH₂—CH₂);

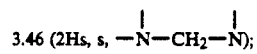
3.46 (2Hs, s, —N—CH₂—N);

6.8–7.2 (3H,m,aromatic protons) ppm.

c) 4,5,6,7-Tetrahydrothieno[3,2-c]pyridine hydrochloride 433 ml of a 6.4N solution of hydrochloric acid in N,N-dimethylformamide are charged into a round bottom flask fitted with a mechanical stirer, a condenser and a thermometer. The solution is heated to 40° C. and 198.7 g of 2-(2-thienyl)ethylamine formimine are added over 30 minutes while the temperature of the reaction mixture is maintained between 45° and 60° C.

The latter is kept stirred for 30 minutes at 60° C. and is then cooled to 0° C. The precipitate is filtered off and is washed with 300 ml of toluene and is then dried at 60° C. under vacuum, which gives a white solid.

227 g of 4,5,6,7-tetrahydrothieno[3,2-c]pyridine hydrochloride are obtained in this manner in a 93% yield.

M.p.: 226° C.

¹H NMR spectrum (DMSO-d₆) (300 MHz)

δ=3.04–3.35 (4H,m); 4.12 (2H,s); 6.92 (1H,d); 7.46 (1H,d); 9.40 (2H,s) ppm.

4,5,6,7-Tetrahydrothieno[3,2-c]pyridine is obtained by making the corresponding hydrochloride basic with 60 ml of aqueous sodium hydroxide and then extracting with 3 times 70 ml of dichloromethane. The organic phases are combined, are washed with 80 ml of water and are then concentrated, and this yields 4,5,6,7-tetrahydrothieno[3,2-c]pyridine.

B.p.: 70°–75° C. (0.5 mm Hg or 66.5 Pa)
Yield: 100%

NMR spectrum (CDCl₃) (300 MHz) δ=2.10 (1H,s); 2.7–3.2 (4H,m); 3.9 (2H,s); 6.72 (1H,d); 7.06 (1H,d) ppm.

d) 5-(2-Chlorobenzyl)-4,5,6,7-tetrahydrothieno[3,2-c]pyridine hydrochloride 26.1 g of 4,5,6,7-tetrahydrothieno[3,2-c]pyridine, 80 ml of ethanol and 19 g of sodium bicarbonate are charged into a 250-ml three-necked round bottom flask fitted with a thermometer, a condenser and a mechanical stirrer. 30.2 g of o-chlorobenzyl chloride are then added and the mixture is heated to about 75°–80° C. during 1 hour. The reaction mixture is evaporated down and the residue is taken up with 200 ml of isopropyl ether. The 5-(2-chlorobenzyl)-4,5,6,7-tetrahydrothieno[3,2-c]pyridine obtained is then added to 100 ml of ethanol. After adding 20 ml of concentrated hydrochloric acid to the ethanolic solution, heating to reflux and cooling the mixture, 46.6 g of 5-(2-chlorobenzyl)-4,5,6,7-tetrahydrothieno[3,2-c]pyridine hydrochloride, which crystallises, are obtained.

M.p.: 210° C.
Yield: 83%.

¹H NMR spectrum (CDCl₃) (300 MHz) δ=3.1–4.9 (8H,m); 6.6 (2H,d); 7.8 (4H,m) ppm.

EXAMPLE B

Preparation of dextrorotatory methyl α-(4,5,6,7-tetrahydro-5-thieno[3,2-c]pyridyl)(2-chlorophenyl)acetate hydrogen sulphate a) Methyl 1-chloro-(2-chlorophenyl)acetate 93.3 g (0.5 mol) of pure 2-chloromandelic acid are mixed with 208 g (1 mol) of phosphorus pentachloride and are heated progressively. The reaction begins at 60° C. and the temperature rises to 100° C.

Heating is continued for 2 h between 120° and 130° C. When the evolution of hydrogen chloride gas has ceased, the mixture is returned to room temperature, is distilled on the water pump and is then taken up with 200 ml of methanol.

The mixture is refluxed for 2 h. The reaction mixture is concentrated by means of a rotary evaporator and is taken up with methylene chloride and water. After phase separation and drying over anhydrous magnesium sulphate, the methylene chloride is stripped off by means of a rotary evaporator, and this yields 121 g of crude ester which is distilled between 80° and 90° C. at a pressure of 0.15 mm Hg (19.95 Pa).

In this way 54.8 g of methyl 1-chloro(2-chlorophenyl)acetate are obtained, assayed at 90% by HPLC (high pressure liquid chromatography).

Yield: 45%.

b) Racemic methyl α-(4,5,6,7-tetrahydro-5-thieno[3,2-c]pyridyl)(2-chlorophenyl)acetate 6 g of potassium carbonate, 7 g of distilled 4,5,6,7-tetrahydrothieno[3,2-c]pyridine (or 15 g of potassium carbonate and 8.8 g of recrystallised 4,5,6,7-tetrahydrothieno[3,2-c]pyridine hydrochloride) are introduced into 80 ml of solvent, followed by 12 g of methyl 1-chloro(2-chlorophenyl)acetate.

The mixture is kept stirred at the temperature shown for the time shown. The solvent is removed under reduced pressure and 50 to 100 ml of water and 100 to 130 ml of ethyl acetate are poured onto the residue. The organic phase is separated off and the aqueous phase is retreated with 30 to 50 ml of ethyl acetate.

The organic phases are combined, are washed with water and are cooled in a bath to −10° C. A mixture of 20 g of ice and 10 ml of concentrated hydrochloric acid is then introduced into the mixture. The final product precipitates. After one hour it is filtered off and dried.

Racemic methyl α-(4,5,6,7-tetrahydro-5-thieno[3,2-c]pyridyl) (2-chlorophenyl)acetate is obtained in this manner.

M.p.: 130°–140° C. (ethyl acetate/isopropanol).

The following yields were obtained, depending on the solvents, temperature and reaction time below:

| Solvent | Temperature (°C.) | Reaction time (h) | Yield (%) |
| --- | --- | --- | --- |
| Tetrahydrofuran | 65 | 20 | 80 |
| Ethyl acetate | 77 | 20 | 81 |
| Isopropyl ether | 65 | 20 | 79 |
| N,N-Dimethylformamide | 75 | 3 | 69 | c) 1-10-Camphosulphonic acid salt of methyl α-(4,5,6,7-tetrahydro-5-thieno[3,2-c]pyridyl) (2-chlorophenyl)acetate 32 g (0.0994 mol) of racemic methyl α-(4,5,6,7-tetrahydro-5-thieno[3,2-c]pyridyl) (2-chlorophenyl)acetate are dissolved in 150 ml of acetone. 9.95 g (0.0397 mol) of laevorotatory 10-camphosulphonic acid monohydrate are added. The homogeneous mixture is left to stand at room temperature. After 48 hours a few crystals appear. The reaction mixture is concentrated to 50 ml and left at room temperature for 24 hours. The crystals obtained are filtered off, washed with acetone and dried (yield: 55% based on the starting racemic).

The crystals thus obtained are redissolved in a minimum volume of boiling acetone (50 ml) and then, after cooling, are filtered off, washed with acetone and dried.

The 1-10-camphosulphonic acid salt of methyl α-(4,5,6,7-tetrahydro-5-thieno[3,2-c]pyridyl) (2-chlorophenyl)acetate is obtained in this manner.

Yield: 88%.

M.p.: 165° C.

$\alpha_D^{20} = +24.75°(c=1.68$ g/100 ml; methanol)

d) Dextrorotatory methyl α-(4,5,6,7-tetrahydro-5-thieno[3,2-c]pyridyl) (2-chlorophenyl)acetate.

800 ml of an aqueous solution of sodium bicarbonate are added to a suspension of 200 g of 1-10-camphosulphonic acid salt of methyl α-(4,5,6,7-tetrahydro-5-thieno[3,2c]pyridyl) (2-chlorophenyl)acetate in 800 ml of dichloromethane. After stirring, the organic phase is separated off and is dried over sodium sulphate and the solvent is removed under reduced pressure to obtain methyl α-(4,5,6,7-tetrahydro-5-thieno[3,2-c]pyridyl) (2-chlorophenyl)acetate in 800 ml of dichloromethane. After stirring, the organic phase is separated off and dried over sodium sulphate and the solvent is removed under reduced pressure to obtain dextrorotatory methyl α-(4,5,6,7-tetrahydro-5-thieno[3,2-c]pyridyl) (2-chlorophenyl)acetate in the form of a colourless oil.

e) Dextrorotatory methyl α-(4,5,6,7-tetrahydro-5-thieno[3,2-c]pyridyl) (2-chlorophenyl)acetate hydrogen sulphate.

The residue obtained above is dissolved in 500 ml of ice-cold acetone and 20.7 ml of concentrated sulphuric acid (93.64%; d=1.83) are added dropwise.

The precipitate which has appeared is isolated by filtration, is washed with 1000 ml of acetone and is then dried in a vacuum oven at 50° C.

139 g of dextrorotatory methyl α-(4,5,6,7-tetrahydro-5-thieno[3,2-c]pyridyl) (2-chlorophenyl)acetate hydrogen sulphate are obtained in this manner in the form of white crystals.

M.p.: 184° C.

$\alpha_D^{20} = +55.1°(c=1.891$ g/100 ml; methanol).

We claim:

1. Isopropyl 2-thienylglycidate of formula:

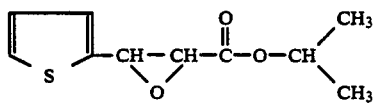

2. Process for the preparation of isopropyl 2-thienylglycidate, characterised in that 2-thienylcarboxaldehyde is reacted with an isopropyl haloacetate in isopropanol and at room temperature, in the presence of an alkali metal isopropylate, and this yields the desired compound.

3. Process according to claim 2, characterised in that the isopropyl haloacetate is isopropyl chloroacetate and the alkali metal isopropylate is sodium isopropylate.

4. Process for the preparation of 2-thienylacetaldoxime, characterised in that,
 a) isopropyl 2-thienylglycidate is saponified with an alkali metal hydroxide at a temperature between room temperature and the reflux temperature of the reaction mixture, to obtain the corresponding alkali metal glycidate,
 b) this alkali metal glycidate is treated, after being or not being isolated from its preparation medium, with an aqueous solution of a hydroxylamine salt, the reaction taking place at room temperature, and this, after a decarboxylation reaction yields the desired compound.

5. Process for the preparation of 2-thienylacetaldoxime, characterised in that:
 a) 2-thienylcarboxaldehyde is reacted in isopropanol and at room temperature to obtain, temporarily and without isolation, isopropyl 2-thienylglycidate,
 b) the glycidate obtained is saponified with an alkali metal hydroxide and at a temperature between room temperature and the reflux temperature of the mixture, and is then treated at room temperature with an aqueous solution of a hydroxylamine salt and this, after a decarboxylation reaction, yields the desired compound.

6. Process for the preparation of thieno[3,2-c]pyridine derivatives of general formula:

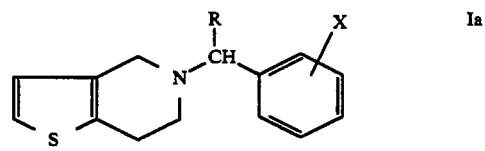

and or their pharmaceutically acceptable salts, in which R denotes hydrogen or a

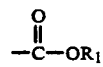

radical in which $R_1$ denotes a $C_1$–$C_4$ alkyl radical and X denotes hydrogen or a halogen atom, characterised in that:
 (a) 2-thienylcarboxaldehyde is reacted in isopropanol and at room temperature to obtain, temporarily and without isolation, isopropyl-2-thienylglycidate,
 (b) the glycidate obtained is saponified with an alkali metal hydroxide and at a temperature between room temperature and the reflux temperature of the mixture, and is then treated at room temperature with an aqueous solution of a hydroxylamine salt and this, after a decarboxylation reaction, yields 2-thienylacetaldoxime,
 (c) this oxime is hydrogenated at a hydrogen pressure of between $10^5$ and $10^7$ Pa, at a temperature of between 20° and 100° C. and in the presence of a basic agent and of a metallic catalyst, to obtain 2-(2-thienyl)ethylamine,
 (d) the ethylamine derivative obtained is reacted with formaldehyde or paraformaldehyde, the reaction being carried out by heating to a temperature of 70° to 90° C. to obtain 2-(2-thienyl)ethylamine formimine,
 (e) the compound thus formed is reacted with an acid and at a temperature of between 40° and 60° C. to obtain a 4,5,6,7-tetrahydrothieno[3,2-c]pyridine salt which is optionally treated with a basic agent to regenerate the thieno[3,2-c]pyridine derivative in basic form,
 (f) 4,5,6,7-tetrahydrothieno[3,2-c]pyridine in base or salt form is reacted, in the presence of an acid-acceptor and optionally under phase transfer conditions, with a compound of general formula:

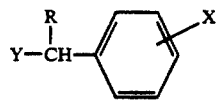

in which R and X have the same meaning as above and Y denotes a halogen atom such as chlorine or bromine or a $C_1$–$C_4$ alkylsulphonate or $C_6$–$C_{10}$ arylsulphonate group, the reaction taking place at a temperature of 60° to 90° C. to obtain the desired thieno[3,2-c]pyridine derivative in basic form which, when R is other than hydrogen, can be separated into its enantiomers in basic form, the basic derivative thus obtained being, if need be, converted into a pharmaceutically acceptable salt by reaction with an appropriate organic or inorganic acid.

7. Process according to claim 4, characterised in that the alkali metal hydroxide is sodium or potassium hydroxide and the hydroxylamine salt is the hydrochloride or the sulphate.

8. Process according to claim 6, characterised in that X denotes chlorine and R denotes hydrogen or a methoxycarbonyl radical.

9. Process according to claim 6, for the preparation of 5-(2-chlorobenzyl)-4,5,6,7-tetrahydrothieno[3,2-c]pyridine.

10. Process according to claim 6, for the preparation of the dextrorotatory enantiomer of methyl α-(4,5,6,7-tetrahydro-5-thieno[3,2-c]pyridyl) (2-chlorophenyl)acetate.

* * * * *